United States Patent
Wilson

(10) Patent No.: US 9,522,916 B2
(45) Date of Patent: Dec. 20, 2016

(54) $A_1$ ADENOSINE RECEPTOR ANTAGONISTS

(76) Inventor: Constance Neely Wilson, Raleigh, NC (US)

(*) Notice: Subject to any disclaimer, the term of this patent is extended or adjusted under 35 U.S.C. 154(b) by 1517 days.

(21) Appl. No.: 13/883,893

(22) PCT Filed: Dec. 19, 2008

(86) PCT No.: PCT/US2008/087638
§ 371 (c)(1),
(2), (4) Date: Oct. 10, 2013

(87) PCT Pub. No.: WO2009/086077
PCT Pub. Date: Jul. 9, 2009

(65) Prior Publication Data
US 2014/0031375 A1    Jan. 30, 2014

Related U.S. Application Data

(60) Provisional application No. 61/008,667, filed on Dec. 21, 2007.

(51) Int. Cl.
*C07D 473/04*     (2006.01)
*C07D 473/06*     (2006.01)

(52) U.S. Cl.
CPC ................................ *C07D 473/06* (2013.01)

(58) Field of Classification Search
CPC .................................................. C07D 473/06
See application file for complete search history.

(56) References Cited

U.S. PATENT DOCUMENTS

| | | | |
|---|---|---|---|
| 4,599,338 A * | 7/1986 | Regnier et al. | 514/234.2 |
| 4,992,474 A | 2/1991 | Skidmore et al. | |
| 5,248,770 A | 9/1993 | Jacobson et al. | |
| 5,268,486 A | 12/1993 | Waggoner et al. | |
| 5,447,933 A * | 9/1995 | Suzuki et al. | 514/263.34 |
| 5,622,649 A | 4/1997 | Hunter et al. | |
| 5,714,494 A | 2/1998 | Connell et al. | |
| 5,719,279 A | 2/1998 | Kufner-Muhl et al. | |
| 5,739,331 A | 4/1998 | Thyrion et al. | |
| 5,786,360 A | 7/1998 | Neely | |
| 5,877,179 A * | 3/1999 | Pollard et al. | 514/263.34 |
| 6,133,445 A | 10/2000 | Waggoner et al. | |
| 6,221,338 B1 | 4/2001 | Staniforth | |
| 6,475,523 B1 | 11/2002 | Staniforth | |
| 6,489,332 B1 | 12/2002 | Neely | |
| 6,521,260 B1 | 2/2003 | Staniforth | |
| 6,582,678 B2 | 6/2003 | Staniforth | |
| 6,599,533 B1 | 7/2003 | Heidlas et al. | |
| 6,680,299 B2 | 1/2004 | Or et al. | |
| 6,680,322 B2 | 1/2004 | Castelhano et al. | |
| 6,680,324 B2 | 1/2004 | Castelhano et al. | |
| 6,941,948 B2 | 9/2005 | Staniforth et al. | |
| 6,948,496 B2 | 9/2005 | Eason et al. | |
| 6,989,155 B1 | 1/2006 | Ganderton et al. | |
| 7,202,252 B2 | 4/2007 | Wilson et al. | |
| 7,247,639 B2 | 7/2007 | Wilson et al. | |
| 7,423,041 B2 | 9/2008 | Wilson et al. | |
| 2003/0170183 A1 | 9/2003 | Staniforth | |
| 2003/0202944 A1 | 10/2003 | Staniforth | |
| 2004/0077645 A1 * | 4/2004 | Himmelsbach et al. | 514/234.5 |
| 2005/0013862 A1 | 1/2005 | Tobyn et al. | |
| 2005/0152849 A1 | 7/2005 | Staniforth | |
| 2005/0158394 A1 | 7/2005 | Staniforth | |
| 2005/0187226 A1 * | 8/2005 | Wilson et al. | 514/263.2 |
| 2005/0205083 A1 | 9/2005 | Staniforth | |
| 2006/0029552 A1 | 2/2006 | Staniforth | |
| 2006/0276378 A1 | 12/2006 | Wilson | |

FOREIGN PATENT DOCUMENTS

| | | | | |
|---|---|---|---|---|
| CA | 2115737 A1 * | 2/1994 | | C07D 401/00 |
| CA | 2115737 | 8/1994 | | |
| CA | 2011329 | 1/1997 | | |
| CA | 2435730 A1 * | 9/2002 | | C07D 473/04 |
| WO | 9616084 A3 | 10/1996 | | |
| WO | 0134610 A1 | 5/2001 | | |
| WO | 03103675 A3 | 3/2004 | | |
| WO | 2004074247 A2 | 9/2004 | | |
| WO | 2005009343 A2 | 2/2005 | | |
| WO | 2007103970 A2 | 9/2007 | | |
| WO | 2009086077 A3 | 10/2009 | | |

OTHER PUBLICATIONS

Byrn, Stephen. Solid-State Chemistry of Drugs, 2d, Chapter 11 Hydrates and Solvates/hydrates, 233-247.*
Morissette, Sherry. Adv. Drug Delivery Rev. 2004, 56, 275-300.*
Rouhi, Maureen. Chem. & Eng. News, 2003, 81(8), 32-35.*
Banker, Gilbert. Modern Pharmaceutics 3rd ed. Marcel Dekker, Inc. New York, 1996.*
Zimmer, Hans. Eur. J. Org. Chem. 1999, 2419-2428.*
Giudice, MR Del. Eur J Med Chem (1996) 31, 59-63.*
Jacobson, Kenneth. Biochemistry (1995) 34, 9088-9094.*
Katsushima, T. J. Med. Chem. 33 (1990) 1906-1910.*
Shimada et al., "8-Polycycloalkyl-1,3-dipropylxanthines as potent and selective antagonists for A1-adenosine receptors", J. Med. Chem., vol. 35, pp. 924-930, XP000002658795, 1992.
Shamim et al., "8-Aryl- and 8-cycloalkyl-1,3-dipropylxanthines: Further potent and selective antagonists for A1 adenosine receptors", J. Med. Chem., vol. 31, pp. 613-617, XP000002658794, 1988.

(Continued)

*Primary Examiner* — Golam M M Shameem
*Assistant Examiner* — Laura Daniel
(74) *Attorney, Agent, or Firm* — James G. Passé; Passé Intellectual Property, LLC

(57) ABSTRACT

This invention relates to compounds of formula (I), Wherein $R_1$-$R_4$ are defined in the Specification, their uses in the practice of medicine, their medicinal formulations, their use in medical diagnosis, and their preparation.

(I)

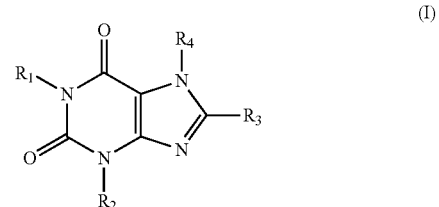

4 Claims, No Drawings

(56) References Cited

OTHER PUBLICATIONS

Corsano, et al. "Structure-Activity Relationship in a Series of 8-Substituted Xanthines as Bronchodilator and A1-Adenosine Receptor Agonists", Arch. Pharm., vol. 328, pp. 654-658, XP000002658796, 1995.

Doytchinova, Irini, "CoMFA-based comaprison of two models of biding site on adenosine A1 receptor", Journal of Computer-Aided Design, 15(1), pp. 29-39, Jan. 2001.

PCT Written Opinion of the International Searching Authority for International Application No. PCT/US2008/087638, International Filing Date Dec. 19, 2008.

Muller, et al., "7-Deaza-2-henyladenines: Structures-Activity Relationships of Potent A1 Selective Adenosine Receptor Antagonists", J. Med. Chem., vol. 33, pp. 2822-2828, 1990.

Smith et al., "March's Advanced Organic Chemistry", 5th Ed., p. 275, et seq., Wiley-Interscience, John Wiley & Sons, New York, 2001.

Higuchi et al., "Prodrugs as Novel Delivery Systems", vol. 14 of the American Chemical Society, Symposium Series, ISBN13: 9780841202917, Jun. 1, 1975.

Roche, Edward ed., "Bioreversible Carriers in Drug Design: Theory and Application", pp. 1-12, American Pharmaceutical Association and Pergamon Press, 1987.

Meyer, et al., "Quantification of Cerebral A1 Adenosine Receptors in Humans Using [18F]CPFPX and PET", Journal of Cerebral Blood Flow & Metabolism 24:323-333, 2004.

Wakabayashi et al., "A PET Study of Adenosine A1 Receptor in the Anesthetized Monkey Brain", Nuclear Medicine & Biology, vol. 27, pp. 401-406, 2000.

Old et al. "Principles of Gene Manipulation: An Introduction to Genetic Engineering", Studies in Microbiology vol. 2, 4th ed, pp. 328-331, Blackwell Scientific Publications, 1989.

Nelson et al., "Lehninger Principles of Biochemistry", 3rd edition, pp. 231-233, Worth Publishers, New York, N.Y., 2000.

\* cited by examiner

$A_1$ ADENOSINE RECEPTOR ANTAGONISTS

FIELD OF THE INVENTION

The present invention concerns compounds useful as $A_1$ adenosine receptor antagonists, along with methods of use thereof.

BACKGROUND OF THE INVENTION

Adenosine receptors are involved in a vast number of peripheral and central regulatory mechanisms such as, for example, vasodilation, cardiac depression, inhibition of lipolysis, inhibition of insulin release and potentiation of glucagon release in the pancreas, and inhibition of neurotransmitter release from nerve endings.

In general, adenosine receptors can be divided into two main classes, $A_1$ receptors which can inhibit, and $A_2$ receptors which can stimulate adenylate cyclase activity. One of the best known classes of adenosine receptor antagonists are the xanthines which include caffeine and theophylline. See e.g., Müller et al., *J. Med. Chem.* 33: 2822-2828 (1990).

In general, many of these antagonists often exhibit poor water solubility, and low potency or lack of selectivity for adenosine receptors. Additionally, selective analogues of adenosine receptor antagonists have been developed through the "functionalized congener" approach. Analogues of adenosine receptor ligands bearing functionalized chains have been synthesized and attached covalently to various organic moieties such as amines and peptides. Attachment of the polar groups to xanthine congeners has been found to increase water solubility. Nonetheless, such developments have yet to fully address problems associated with potency and selectivity.

SUMMARY OF THE INVENTION

In one aspect, the invention is a compound of the general formula (I):

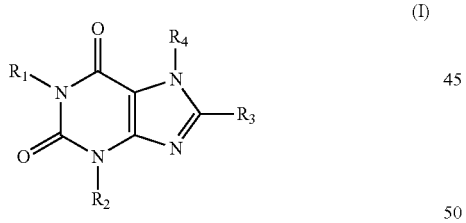

wherein;
$R_1$ is $C_{1-8}$ straight or branched, optionally unsaturated, hydrocarbon moiety optionally substituted with one or more $OR_5$, $NR_5R_6$, $SO_3H$, $PO_3H_2$, $COOR_7$, $NR_8R_9NR_{10}COR_{11}$, $Alk_1COOR_{12}$, $SO_2R_{13}$, $Alk_2NR_{14}R_{16}$, $Alk_3OH$, or halogen groups,
  wherein
    $R_5$ to $R_{15}$ are independently H or $C_{1-8}$ straight or branched, optionally unsaturated, hydrocarbon chain,
    $Alk_1$ through $Alk_3$ are independently $C_{1-8}$ straight or branched alkylene or alkenylene;
$R_2$ is $L_1G_1$,
  wherein;
    $L_1$ is a $C_{1-20}$ straight or branched, optionally unsaturated, hydrocarbon chain moiety;
    $G_1$ is a H, $OR_{16}$, $NR_{17}R_{18}$, $PO_3H_2CONR_{19}R_{20}$, $COOR_{21}$, $NR_{22}COAlk_4NR_{23}R_{24}$, $NR_{26}COAlk_6NR_{26}Alk_6NR_{27}R_{28}$, $OCOC_6H_4SO_2F$, $NHCOC_6H_4SO_2F$; or a $C_{3-11}$ hydrocarbon, optionally bridged, optionally aromatic, optionally unsaturated, ring optionally substituted with one or more groups selected from
      $SO_3H$, $PO_3H_2$, halogen, $OR_{29}$, $COOR_{30}$, $NO_2$, $NR_{31}R_{32}$, $NR_{33}COR_{34}$, $NR_{36}COAlk_7NR_{36}R_{37}$, $NR_{38}COAlk_8CONR_{39}Alk_9NR_{40}R_{41}$, $NR_{42}COAlk_{10}COAlk_{11}NR_{43}R_{44}$, $Alk_{12}NR_{45}COAlk_{13}NR_{46}R_{47}$, $Alk_{14}NR_{48}COAlk_{15}CONR_{49}Alk_{16}NR_{50}R_{51}$, $Alk_{17}COOR_{52}$, $Alk_{18}COAlk_{19}NR_{53}R_{54}$, $SO_2R_{55}$, $SO_2F$, $Alk_{20}OR_{56}$, $Alk_{21}NR_{57}R_{58}$, $Alk_{22}COAlk_{23}CONR_{59}Alk_{24}NR_6OR_{61}$ or $Alk_{25}COOR_{62}$;
  wherein;
    $Alk_4$-$Alk_{25}$ are independently $C_{1-8}$ straight or branched alkylene or alkenylene;
    $R_{16}$-$R_{62}$ are independently H or $C_{1-8}$ straight or branched alkyl;
$R_3$ is $L_2G_2$,
  wherein;
    $L_2$ is a $C_{1-8}$ straight or branched, optionally unsaturated, hydrocarbon moiety optionally substituted with one or more, water soluble, polar groups selected from
      $OR_{63}$, $NR_{64}R_{65}$, $SO_3H$, $PO_3H_2$, $COOR_{66}$, $NR_{67}R_{68}NR_{69}COR_{70}$, $Alk_{26}COOR_{71}$, $SO_2R_{72}$, $Alk_{27}NR_{73}R_{74}$, $Alk_{28}OH$, or halogen; and when $L_2$ is $C_{2-8}$, $L_2$ may be intraspersed with one or more hetero atoms;
    $G_2$ is one or two $C_{3-11}$ non-aromatic, non-bridged, cyclic hydrocarbons, which independently may have one or more hetero atoms and which may be optionally substituted with one or more groups selected from
      $SO_3H$, $PO_3H_2$, halogen, $OR_{75}$, $COOR_{76}$, $NO_2$, $NR_{77}COR_{78}$, $Alk_{29}COOR_{79}$, $SO_2R_{80}$, $Alk_{30}NR_{81}R_{82}$, H, OH, $Alk_{31}OH$, $Alk_{32}NR_{83}R_{84}$, $NR_{85}CONR_{86}R_{87}$, or $Alk_{33}COOH$, $Alk_{34}H$, and $NR_{88}R_{89}$; and epoxides thereof,
  wherein;
    $Alk_{26}$-$Alk_{34}$ are independently $C_{1-8}$ straight or branched alkylene or alkenylene,
    $R_{63}$-$R_{89}$ are independently H or $C_{1-8}$ straight or branched alkyl;
$R_4$ is $C_{2-8}$ alkyl, $Alk_{35}COOH$, $Alk_{36}COOR_{90}$, $Alk_{37}CONR_{91}R_{92}$, $Alk_{38}OH$, $Alk_{39}SO_3H$, $Alk_{40}PO_3H_2$, $Alk_{41}OR_{93}$, $Alk_{42}OH$ or $Alk_{43}NR_{94}R_{95}$, or, $Alk_{44}NR_{96}Alk_{45}OH$; and $R_4$ may also be H or methyl when $R_3$ is other than dicycloalkylmethyl,
  wherein;
    $Alk_{35}$ through $Alk_{45}$ are independently $C_{1-8}$ straight or branched alkylene or alkenylene;
    $R_{90}$ through $R_{96}$ are independently H, or $C_{1-8}$ straight or branched alkyl; and
  when $R_4$ is other than H, methyl, alkyl, $Alk_{35}COOH$, $Alk_{36}COOR_{90}$, $Alk_{39}SO_3H$, $Alk_{41}OR_{93}$, or $Alk_{42}OH$, $G_2$ may include bridged cyclic hydrocarbons; and
salts, solvates, and prodrugs thereof.

Also within the scope of the first aspect is a compound of formula (I) that has one or more radioactive or non-radioactive label moieties wherein the label moieties are optionally connected to the compound through one or more spacer moieties; and salts, solvates and hydrates thereof.

Of further interest are the compounds of formula (I) wherein:
- $R_1$ is $C_{1-4}$ straight or branched alkylene optionally substituted with $OR_4$, $NR_5R_6$, or $COOR_7$,
- $L_1$ is a $C_{1-8}$ straight or branched alkylene,
- $G_1$ is H, $OR_{16}$, $NR_{17}R_{18}$, $CONR_{19}R_{20}$, $COOR_{21}$, $OCOC_6H_4SO_2F$, or $NHCOC_6H_4SO_2F$; or a $C_{3-11}$ hydrocarbon, optionally bridged, optionally aromatic, optionally unsaturated, ring.
- $L_2$ is a $C_{1-4}$ straight or branched hydrocarbon chain,
- $G_2$ is a $C_{3-11}$ non-aromatic, non-bridged, cyclic hydrocarbon, optionally having one or more hetero atoms, optionally substituted by one or more groups selected from
  halogen, $OR_{75}$, $COOR_{76}$, $NO_2$, $NR_{77}COR_{78}$, $Alk_{29}COOR_{79}$, $SO_2R_{80}$, $Alk_{30}NR_{81}R_{82}$, H, OH, $Alk_{31}OH$, $NR_{85}R_{86}$, $CONR_{86}R_{87}$, and $Alk_{34}H$; and epoxides thereof.
- $R_4$ is H, $Alk_{40}PO_3H_2$, $Alk_{43}NR_{94}R_{95}$, or $Alk_{44}NR_{96}Alk_{45}OH$.

Of particular interest are the compounds of formula (I) wherein:
- $R_1$ is $C_{1-4}$ straight or branched hydrocarbon moiety.
- $L_1$ is ethylene, or propylene, or butylene,
- $G_1$ is cyclopropyl, cyclopentyl, cyclohexyl, cyclohexenyl bornyl, norbornyl, adamantyl, noradamantyl, bicyclooctyl, phenyl, substituted, naphthyl, $OCOC_6H_4SO_2F$, or $NHCOC_6H_4SO_2F$
- $L_2$ is methylene, ethylene, or propylene,
- $G_2$ is cyclopropyl, cyclopentyl, cyclohexyl, cyclohexenyl, or decalin,
- $R_4$ is H or $Alk_{44}NR_{96}Alk_{46}OH$.

A second aspect is a method of treating $A_1$ adenosine receptor related disorders in a mammal, including a human, comprising administering an effective therapeutic amount of a compound of formula (I) or a salt, solvate or prodrug to the mammal in need there of.

A third aspect provides a pharmaceutical composition, which comprises a compound of formula (I) and a pharmaceutically acceptable carrier.

A fourth aspect provides for diagnostic assay-type probes of a compound of formula (I), wherein the probes are labeled or conjugated with radioactive or non-radioactive material.

A fifth aspect is the use of a compound of formula (I) as an imaging agent in diagnostic procedures such as MRI and PET.

A sixth aspect is the use of a compound of formula (I) in a cell or receptor based assay.

A seventh aspect is the preparation of a compound of formula (I) for use as a medicament.

DETAILED DESCRIPTION OF EMBODIMENTS OF THE INVENTION

The present invention will now be described more fully hereinafter, in which embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

While the present invention is intended primarily for the treatment of human subjects, it will be appreciated that other subjects, particularly mammalian subjects such as dogs, cats, horses, rabbits, etc., can also be treated by the methods of the present invention for veterinary purposes.

"Halogen" as used herein refers to any suitable halo group, such as fluorine, chlorine, bromine, and iodine. A "bridged cyclic hydrocarbon" is a cyclic, i.e. "ring," hydrocarbon compound having one or more hydrocarbon chains, i.e. "bridges," connecting two or more carbon atoms of the cyclic hydrocarbon compounds. Examples of bridged cyclic hydrocarbons include bicyclic, tricyclic, tetracyclic, pentacyclic compounds, and the like. Cyclic hydrocarbons include fused compounds, i.e. two or more cyclic hydrocarbon that share one or more bonds such as decalin.

Compounds as described above may be prepared in accordance with the techniques known in the art such as described in U.S. Pat. Nos. 5,719,279; 5,786,360; 5,739,331; 6,489,332; 7,202,252; 7,247,639; and 7,423,041 the techniques described in the Examples below; and variations of the foregoing that will be understandable to those skilled in the art of synthetic organic chemistry in light of the disclosure herein.

The compounds of formula (I) may form salts having pharmaceutically compatible counterions with both organic and inorganic acid and bases. Likewise, many of the compounds of formula (I) may form solvates including hydrates. Such pharmaceutically acceptable base addition salts are those salts that retain the biological effectiveness and properties of the free acids, and that are obtained by reaction with suitable inorganic or organic bases. While pharmaceutically acceptable salts and solvates are useful for the treatment of mammals, including humans, non-pharmaceutically salts and solvates may be useful as chemical intermediates, and thus, are within the scope of the present invention. The salts are prepared by contacting the free base form of the compound with an appropriate amount of the desired acid in a manner known to one skilled in the art.

Exemplary weak organic acids for salt formation include but are not limited to acetic acid, beta-alanine, dl-alanine, D-alanine, L-alanine, formic acid, propanoic acid, butyric acid, palmetic acid, oleic acid, sebacic acid, cinnamic acid, adipic acid, citric acid, ascorbic acid (vitamin C), lactic acid, malic acid, maleic acid, fumaric acid, tartaric acid, dl-glutamic acid, D-glutamic acid, L-glutamic acid, dl-aspartic acid, D-aspartic acid, L-aspartic acid, glycine, succinic acid, glutaric acid, gluconic acid, benzoic acid, p-chlorobenzoic acid, p-hydroxybenzoic acid, p-methoxybenzoic acid, o-hydroxybenzoic acid (salicylic acid), 1-hydroxy-2-naphthoic acid, 3-hydroxy-2-naphthoic acid, and the like. Strong organic acids that may be used for salt formation include, for example, benzenesulfonic acid, p-toluenesulfonic acid, m-nitrobenzenesulfonic acid, methanesulfonic acid, ethanesulfonic acid, 1-naphthalenesulfonic acid, 2-naphthalenesulfonic acid, laurylsulfonic acid, and the like. Examples of strong inorganic acids for salt formation include hydrochloric acid, hydrobromic acid, hydroiodic acid, sulfuric acid, phosphoric acid, nitric acid, sodium bisulfate, potassium bisulfate, sodium hydrogen phosphate, potassium hydrogen phosphate, boric acid, xinafoic acid (i.e., xinafoate salt is formed with 1-hydroxy-2-naphthoic acid) and the like.

Xinafoate salts, such as salmeterol xinafoate, are known and have been synthesized in the art. See, for example, Merck Index, supra, and U.S. Pat. No. 4,992,474, both of which are herein incorporated by reference in their entirety. Because xinafoate salts are known to be largely insoluble and to exhibit reduced oral absorption, such salts may be particularly potent, safe, and efficacious when administered by pulmonary inhalation. Inhalational therapy with a xinafoate salt of an $A_1$ adenosine receptor antagonist of the invention may minimize negative systemic effects associated with the traditional $A_1$ adenosine receptor antagonist agents. Inhalation of the $A_1$ adenosine receptor antagonists of the invention as xinafoate salts may permit more direct contact with the therapeutic agent and the lung.

Examples of suitable bases for pharmaceutically acceptable salt formation include, but are not limited to, ammonium hydroxide, sodium hydroxide, sodium carbonate, sodium bicarbonate, potassium hydroxide, calcium hydroxide, ammonia, organic amines such as triethylamine, and the like. The salts may be prepared by contacting the free acid form of the compound with an appropriate amount of the desired base in a manner known to one skilled in the art. An example of a suitable solvate is a hydrate. Solvates may be prepared by any appropriate method of the art.

The compounds of formula (I) may be administered per se or in the form of acid or basic salts, hydrates, solvates and pro-drugs thereof, in accordance with known techniques, to carry out the methods described herein. The term "prodrug" refers to compounds that are transformed in vivo to yield the parent compound of the above formulae, for example, by hydrolysis in blood. A thorough discussion is provided in T. Higuchi and V. Stella, Prodrugs as Novel Delivery Systems, Vol. 14 of the A.C.S. Symposium Series and in Edward B. Roche, ed., Bioreversible Carriers in Drug Design, American Pharmaceutical Association and Pergamon Press, 1987. See also U.S. Pat. No. 6,680,299. Examples include, but are not limited to, a prodrug that is metabolized in vivo by a subject to an active drug having at least some of the activity of the active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The compounds of the present invention can be useful in diagnostic assays. Accordingly, the invention also provides $A_1$ adenosine receptor antagonist compounds with radioactive or non-radioactive labels suitable for executing such assays. Labeled compounds are useful as assay-type probes or conjugates, and to obtain quantitative binding measurements of the $A_1$ adenosine receptor antagonist compounds. As used herein, the term "assay-type probes" refers to those materials which are useful for enhancing the selectivity of the quantitative analysis of the $A_1$ adenosine receptor compounds of the invention.

Examples of such assay-type probes and their diagnostic uses are described in Jacobson, et al., U.S. Pat. No. 5,248,770 (770). The probes are—useful because they have little adverse effect on the affinity of the compounds of the present invention. Nuclear markers (also referred to a "labels") include, but are not limited to, nuclear spin markers, e.g. a $^{19}F$ MRI probe, radioactive markers, e.g., $^{18}F$, $^{11}C$, $^{15}N$, $^{125}I$, $^{14}C$, $^{15}O$ and $^3H$ (tritium) isotope marker, and complexes of metal atoms or metal ions and chelating agents. Typically, the metal or metal ion in the complex will have a heavy, radioactive nucleus. The marker atoms may be chemically bonded to, or complexed, e.g. chelated, with, a compound of formula (I) or may be one of the integral carbon or heteroatom of a compound of formula (I).

Such labeled compounds can be used for in vitro or in vivo imaging of adenosine receptors, especially in tissues, including but not limited to the brain, heart, liver, kidney, and lungs to obtain quantitative measurements of adenosine receptors and determine the distribution and regional binding characteristics of adenosine receptors in tissue. These assay-type probes may be used, inter alia, in connection with such diagnostic techniques as magnetic resonance imaging (MRI) and positron emission tomography (PET). See, for example, Myer, et al., Quantification of cerebral A1 Adenosine Receptors in Humans Using [$^{18}F$]CPFPX and PET. *J Cerebral Blood Flow & Metabolism* 24:323-333, 2004 and Wakabayashi, et al., A PET Study of Adenosine A1 Receptor in the Anesthetized Monkey Brain, *Nuclear Med & Biol* 27:401-406, 2000. An exemplary metal ion is a radioactive isotope of technetium or indium. An exemplary chelating agent is diethylenetriamine pentaacetic acid.

Various non-radioactive materials can be used in labeling the present $A_1$ adenosine receptor compounds. Numerous examples are presented in U.S. Pat. No. 5,248,770. Biotin is a well known non-radioactive label for such probes, as described in R. W. Old et al. *Principals of Gene Manipulation*, 4th ed: 328-331 (1989). To facilitate labeling the compounds with biotin or any other appropriate label, a spacer component or moiety may be added to a compound of the present invention by any suitable method taught in the art, e.g. see U.S. Pat. No. 5,248,770. Exemplary spacer moieties include, but are not limited to, an oligopeptide, triglycidyl, N-hydroxysuccinimide ester, succinimidyl-thiohexane (6-thiohexyl-3-amidocarboxypropanoyl), succinimidyl hexamethyleneamine (6-aminohexyl-3-amidocarboxypropanoyl), succinimidyl-cadaverine (5-aminopentyl-3-amidocarboxypropanoyl), and succinimidyl-hexylmaleimide (6-N-maleimidohexyl-3-amidocarboxypropanoyl).

A non-radioactive label, e.g., biotin, may be bonded to any suitable linkage provided by substituents on the compound structure in accordance with any suitable technique taught in the art. For example, referring to the compounds of formula (I) as defined herein, biotin may be bonded to one or more of the hydroxy groups, amino groups or carboxyl groups present such as at the $R_1$ through $R_3$ positions on the compound. Additionally, the biotin may be bonded to one or more of the hydroxyl groups that may be present at the $R_1$ through $R_3$ positions on the compound. The biotin-labeled probes may be detected through appropriate and known analytical techniques Fluorescent compounds, typically fluorescent dyes, may also be employed as a non-radioactive labels and are applied to appropriate locations on the compounds of the invention as described above. Such dyes include, but are not limited to, tetramethylrhodamine, fluorescein isothiocyanate, Cy3, (see Waggoner, et al., U.S. Pat. No. 5,268,486, Dec. 7, 1993) or Cy3B (see Waggoner et al., U.S. Pat. No. 6,133,445, Oct. 17, 2000) and mixtures thereof. Other non-radioactive materials include for example, nitrobenzoxadiazole; 2,2,6,6-tetramethyl-piperindinyloxy-4-isothiocyanate; luminescent dyes;

obelin; and mixtures thereof, which may be applied in an analogous manner as fluorescent compounds.

The skilled artisan will appreciate that also within the scope of the invention is the use of the compounds of formula (I) marked with a radioactive or non-radioactive label in in vitro assays. For example, such marked compounds may be used in clinical cell-based assays and in receptor-based assays. Such assays include, but are not limited to, radioligand binding assays, high throughput screening assays, and flow cytometry based assays, for example fluorescence-activated cell sorting (FACS) based assays. Examples of such assays include, but are not limited to, radioimmunoassay and enzyme-linked immunosorbent assays (ELISA) (see, e.g., Nelson, et al., *Lehninger Principles of Biochemistry*, 231, Worth, N.Y., (2000).

The invention is also directed to pharmaceutical compositions which include compounds of the present invention and a pharmaceutically acceptable carrier. The pharmaceutical compositions described herein can be prepared by any applicable method of the art. The pharmaceutical composition is particularly useful in applications relating to organ preservation in vivo or in situ, perfusion of an isolated organ either removed or contained within the body (e.g., when an organ is transported for transplantation), cardiopulmonary bypass, perfusion of an extremity or limb, and the like. The compounds may be used in intra-articular, intra-thecal, gastrointestinal, and genital urinary applications, as well as in any cavity or lumen such as, for example, the thoracic cavity or ear canal.

While the present invention is intended primarily for the treatment of human subjects, it will be appreciated that other subjects, particularly mammalian subjects such as dogs, cats, horses, rabbits, etc., can also be treated by the methods of the present invention for veterinary purposes The pharmaceutical compositions may be employed, as an example, in oral dosage form as a liquid composition. Such liquid compositions can include suspension compositions or syrup compositions and can be prepared with such carriers as water; a saccharide such as sucrose, sorbitol, fructose, and the like; a glycol such as polyethyleneglycol, polypropyleneglycol, and the like; an oil such as sesame oil, olive oil, soybean oil, and the like; an antiseptic such as p-hydroxybenzoic acid esters and the like; and a flavor component such as a fruit flavor or a mint flavor.

Liquid pharmaceutical compositions also include emulsions of the active ingredient and one or more excipients with a pharmaceutically acceptable polymer, such as polyethylene glycol. For example, see Hunter, et al., U.S. Pat. No. 5,622,649. Likewise, within the scope of the present invention, the active ingredient and excipients may be formulated as an anhydrous, homogeneous suspension in one or more phospholipids, or other compounds having similar physical and pharmacological properties. See, for example, Heidlas, et al., U.S. Pat. No. 6,599,533.

The pharmaceutical compositions may also be in the form of powder, tablets, capsules, and tablets and can be prepared with various carriers. Suitable carriers include, but are not limited to, lactose, glucose, sucrose, mannitol, and the like; disintegrators such as starch, sodium alginate, and the like; binders such as polyvinyl alcohol, hydroxypropyl cellulose, gelatin, and the like; surfactants such as, for example, fatty acid esters; and plasticizers such as, for example, glycerins. The composition of the present invention is especially useful when applied sublingually. It should be noted that in the preparation of the tablets and capsules, a solid pharmaceutical carrier is used. Advantageously, the pharmaceutical compositions may be used in the form of, for example, eye drops or an aerosol.

Other types of pharmaceutical compositions may be employed in the form of a suppository, a nasal spray, and an injectable solution. These compositions are prepared using appropriate aqueous solutions, which may include, but are not limited to, distilled water, and saline and buffer additives. Other components may be employed such as organic materials including neutral fatty bases. Additionally, the pharmaceutical compositions may be utilized in a transdermal application.

For administration by inhalation, $A_1$ adenosine receptor antagonists of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch. Methods and devices for administering compositions via pulmonary inhalation and for producing particles suitable for such administration are disclosed in the art. See, for example, U.S. Pat. Nos. 6,221,338, 6,475,523, 6,521,260, 6,582,678, 6,941,948, 6,948,496, 6,989,155; U.S. Patent Application Publication Nos. 2003/0170183, 2003/0202944, 2005/0013862, 2005/0152849, 2005/0158394, 2005/0205083, and 2006/0029552; all of which are herein incorporated by reference in their entirety.

Biopolymers may be used as carriers in the above pharmaceutical compositions. Exemplary biopolymers may include, for example, proteins, sugars, lipids, or glycolipids.

The $A_1$ receptor antagonists of the present invention are particularly useful as, for example, anti-allergenics, anti-inflammatory agents, CNS stimulants, diuretics, anti-asthmatics, cardiotonics, coronary vasodilators, and anti-tussives and as agents for the treatment of viral or retroviral infections and immune deficiency disorders such as acquired immunodeficiency syndrome (AIDS).

The present invention also provides methods of treating $A_1$ adenosine receptor related disorders, including, but not limited to, disorders of the respiratory, cardiac, central nervous system, kidney, liver, and immune system, such disorders including, but not limited to, congestive heart failure, hypertension, such as systemic hypertension and pulmonary hypertension, ischemia-reperfusion organ injury, endotoxin-related tissue injury, renal failure (acute or chronic) and renal insufficiency or impairment, edematous disorders, including, but not limited to, ascites associated with cirrhosis of the liver, degenerative disorders of the nervous system, including, but not limited to, Alzheimer's disease and multiple sclerosis, depression, obesity, asthma, diabetes, osteoporosis, apnea, bradycardia, cardiopulmonary resuscitation, cystic fibrosis, allergic conditions, including, but not limited to allergic rhinitis and anaphylactic shock, autoimmune disorders, inflammatory disorders, chronic obstructive pulmonary disorders, chronic cough, coronary artery disease, biliary colic, postoperative ileus, fibrosis, sclerosis, hemorrhagic shock, Adult Respiratory Distress Syndrome (ARDS), Acute Lung Injury (ALI), Severe Acute Respiratory Syndrome (SARS), septicemia, substance abuse, alcohol abuse, dependence, or addiction, drug abuse, dependence, or addiction, Parkinson's disease, and acquired immunodeficiency syndrome (AIDS), traumatic brain damage, neonatal brain damage, including, but not limited to, that associated with birth, sepsis, pneumonic plague, plague sepsis, chronic bronchitis, pulmonary fibrosis, bronchopulmonary dysplasia, emphysema, bronchiolitis obliterans (or bronchiolitis obliterans syndrome), and airway remodeling.

The dosage of the active agent will depend upon the condition being treated, the age and condition of the subject, the route of administration, etc. In general, the dosage can be determined in accordance with known techniques. In one embodiment, the dosage of the active agent may, for example, be from 1 or 10 to 300 or 800 mg per adult subject.

The compounds described herein may be used alone or in combination with other compounds for the treatment of the disorders described herein, including, but not limited to, those compounds described in PCT Application, WO 03/103675, published Dec. 18, 2003.

Other compounds for the treatment of $A_1$ adenosine related disorders described herein include, for example, antibiotics, anti-viral agents, anti-fungal agents, other bronchodilators, including beta-2 adrenergic receptor agonists, anti-cholinergics, anti-histamines, phosphodiesterase (PDE) inhibitors, particularly PDE-IV (PDE-4) inhibitors, leukotriene receptor antagonists, anti-inflammatory agents including but are not limited to glucocorticoids, cromolyn, and nonsteroidal anti-inflammatory drugs, mast cell stabilizers such as cromoglycate, surfactants, corticosteroids, such as beclomethasone dipropionate, fluticasone propionate, fluticasone furoate, $P_{2X}$ purinoceptor antagonists, $P_{2Y}$ purinoceptor agonists, $A_{2b}$ adenosine receptor antagonists, $A_{2a}$ adenosine receptor agonists, $A_3$ adenosine receptor agonists, other xanthines, $A_1$ adenosine receptor antagonists, $A_3$ adenosine receptor antagonists, anticytokines, 5-lipoxygenase inhibitors, platelet activating factor antagonists, thromboxane receptor antagonists, chemokine antagonists, such as VLA 4 antagonists and CCR-1 antagonist, neurokinin receptor antagonists, inhibitors of B cells, T cells, Leukocyte Selective Anti-inflammatory Drugs (LSAIDs), adhesion molecule antagonists, immunomodulators, such as lipopolysaccharide or Bacillus Calmette Guerin (BCG), immunosuppressants, adenosine production inhibitors, tryptase inhibitors, vaccines, complement inhibitors, kinase inhibitors, JAK kinase inhibitors, JAK 3 inhibitors, serine kinase inhibitors, respiratory antisense oliogonucleotides (RASON), diuretics, cardiotonics, cognition enhancers, cholesterol, lipid, and triglyceride lowering drugs, statins, and anti-sepsis treatments.

As used herein, "effective amount" or "effective therapeutic amount" refers to a nontoxic but sufficient amount of the compound to provide the desired pharmacological effect, including but not limited to, improvement in the condition of the subject (e.g., in one or more symptoms), delay in the progression of the condition, prevention or delay of the onset of the disease or illness, etc.

As pointed herein, the exact amount required will vary from subject to subject, depending on age, general condition of the subject, the severity of the condition being treated, the particular biologically active agent administered, and the like. An appropriate "effective" amount in any individual case may be determined by one of ordinary skill in the art by reference to the pertinent texts and literature and/or by using routine experimentation.

An effective amount of a prodrug of the present invention is the amount of prodrug that must be metabolized within the body of a mammal, such as a human, to yield an effective amount of a compound of formula (I).

The present invention relates to methods of treating $A_1$ adenosine receptor-related disorders, comprising concurrently administering an $A_1$ adenosine receptor antagonist as described above with at least one additional active agent such as described above effective to treat $A_1$ adenosine receptor-related disorders, wherein the $A_1$ adenosine receptor-related disorder is as described above.

Administration of compounds in combination may be carried out in like manner as described above, with the active compound and the additional active agent being administered in the same or different carrier. Pharmaceutical formulations containing such combinations of active agents may also be prepared in like manner as described above.

As noted herein above, compounds of formula (I) may be made by any method known in the art of organic chemistry. However, they may be conveniently prepared according the method of Scheme 1. Those skilled in this art will appreciate that certain modifications to Scheme 1 may be appropriate depending on the nature of $R_1$, $R_2$, or $R_3$. For examples, blocking and deblocking of sensitive groups, such as amino groups, in connections with one or more steps according to standard procedures well known to the artisan may be desirable. Further, other standard processes and procedures within the repertoire of the artisan such as oxidation, reduction, and hydrolysis, might need to be employed in the course of the synthesis of a compound of formula (I) using Scheme 1.

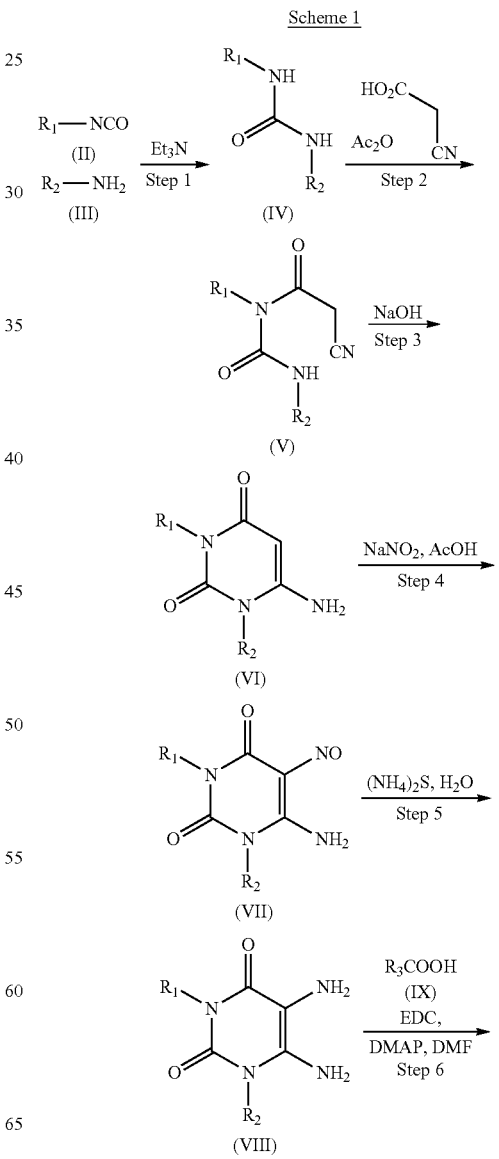

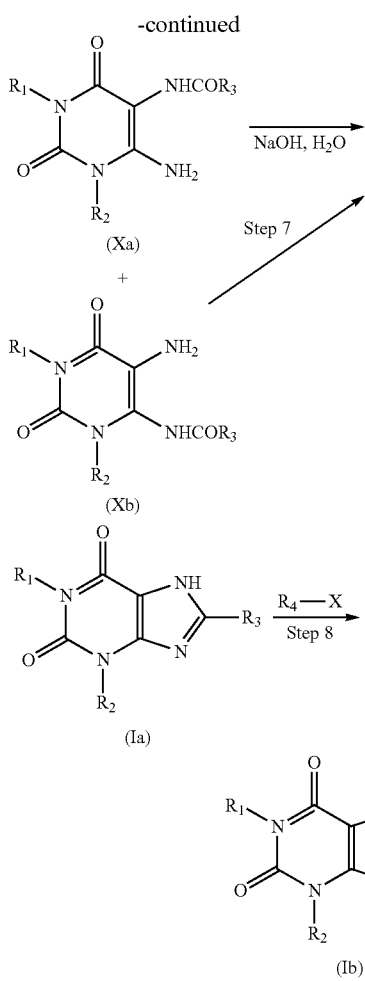

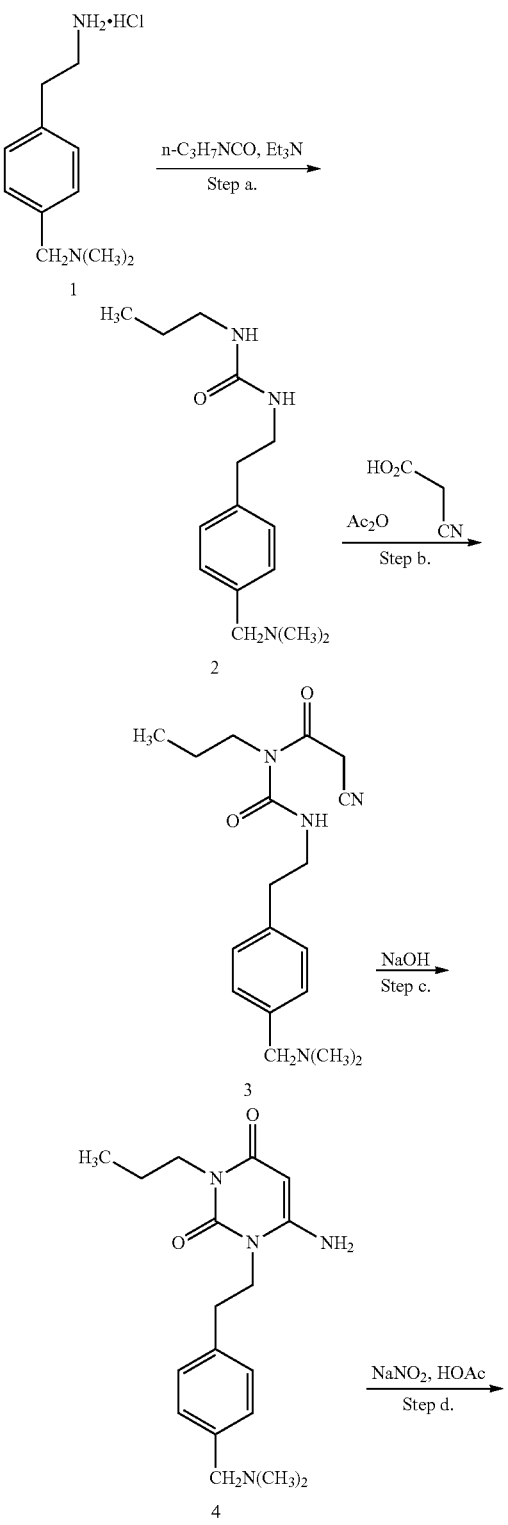

In Step 1 of Scheme 1, an isocyanate of formula (II) bearing an $R_1$ group is reacted with an amino compound of formula (III) bearing an $R_2$ group in the presence of an aprotic base such as a tertiary amine, e.g. triethyl amine, to yield the urea compound of formula (IV). In Step 2, compound (IV) is reacted with cyanoacetic acid in the presence of acetic anhydride yielding the compound of formula (V), which, in Step 3, is subsequently treated with a metal hydroxide such as sodium hydroxide to produce the compound of formula (VI). The compound of formula (VI) is converted into the compound of formula (VII) by treatment with sodium nitrite and acetic acid in Step 4.

In Step 5, diammonium sulfide in water yields the diamino compound of formula (VIII). In turn, in Step 6, Compound (VIII) is reacted with the carboxylic acid of formula (IX) bearing $R_3$ in dimethylformamide (DMF) and in the presence of 1-(3-dimethylaminopropyl)-3-ethylcarbodiimide HCl (EDC) and 4-dimethylaminopyridine (DMAP) to produce the two isomeric compounds (Xa) and (Xb). In Step 7, treatment of compounds (Xa) and (Xb) with a strong alkali hydroxide, such as sodium hydroxide, yields the compound of formula (Ia) wherein $R_4$ is hydrogen.

Compounds of formula (I) wherein $R_4$ is other than hydrogen, i.e., the compounds of formula (Ib), may be prepared by any suitable means known in the art in Step 8. For example, a compound of formula (Ia) may be reacted with $R_4$—X wherein X is a leaving group. (Leaving groups, their utility, and means of their employment in synthetic organic chemistry are well known in the art and explained in University level organic chemistry text books. For example, see M. Smith and J. March, *March's Advanced Organic Chemistry*, 5$^{th}$ Ed., page 275, et seq., Wiley-Interscience, John Wiley & Sons, New York (2001)). Alternatively, $R_4$ may be introduced prior to Step 7 and any means of the art.

The present invention is explained in greater detail in the following non-limiting Examples.

Example 1

Synthesis of 5,6-Diamino-1-[2-(4-(dimethylamino)methylphenyl)ethyl]-3-propyluracil (6)

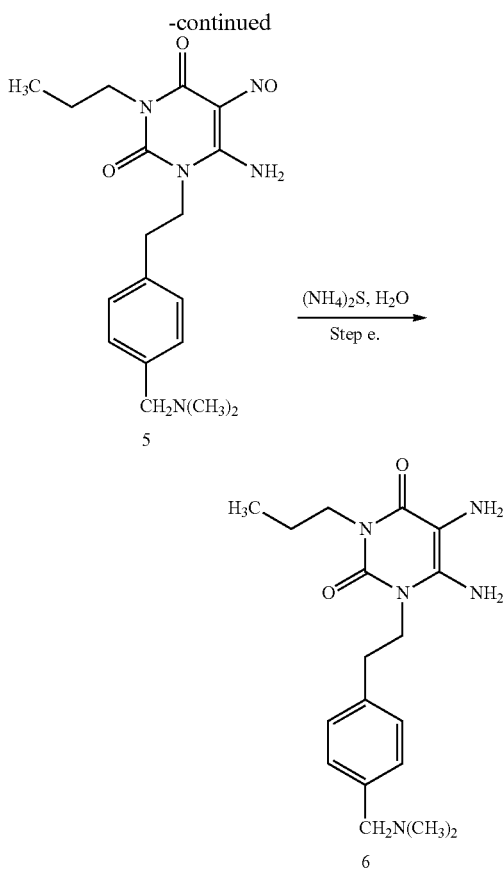

Step a: Conversion of 4-(dimethylamino)methyl-phenethylamine Hydrochloride (1) to 1-[2-(4-(dimethylamino)methylphenyl)ethyl]-1'-propylurea (2)

To a slurry of 785 gm of 4-(dimethylamino)methyl phenethylamine hydrochloride (1) and 11.2 L of toluene is added slowly, 620 mL of triethylamine and this mixture is stirred for 30 min. at room temperature. To this suspension is then added slowly, 398 mL of n-propyl isocyanate, and the mixture is stirred overnight at room temperature to give a solid precipitate. The heterogeneous mixture is filtered and the isolated solids are washed with 1.5 L of toluene and then air dried. The crude product is stirred with 6 L of water to dissolve residual triethylamine hydrochloride. The solids are isolated by filtration and air dried. This material is dissolved in 4 L of absolute ethanol and 1 L of water is added to induce crystallization. The solids are filtered, washed with 2 L of 1:1 ethanol-water and air dried to yield a first crop of gm of 1-[2-(4-(dimethylamino)methyl phenyl)ethyl]-1'-propylurea (2). The recrystallization mother liquors yielded an additional 1-[2-(4-(dimethylamino)methylphenyl)ethyl]-1'-propylurea (2).

Step b: Conversion of 1-[2-(4-(dimethylamino) methyl phenyl)ethyl]-1'-propylurea (2) to 1'-Cyanoacetyl-1-[2-(4-(dimethylamino)methyl phenyl)ethyl]-1'-propylurea (3)

A thick mixture of 925 gm of 1-[2-(4-(dimethylamino) methylphenyl)ethyl]-1'-propylurea (2) and 1.0 L of acetic anhydride is stirred and warmed to ca. 50 degrees C. To this mixture is added 343.2 gm of cyanoacetic acid and 0.5 L of acetic anhydride and this homogeneous mixture is stirred at 80-85 degrees C. for three hours. The mixture is cooled and concentrated under vacuum to remove acetic acid and residual acetic anhydride. The residue is triturated successively with 1.0 L portions of water, acetonitrile, toluene and ethyl acetate. The residue is then dried under vacuum to yield 1261 gm of a 2:1 mixture of 1'-cyanoacetyl-1-[2-(4-(dimethylamino)methylphenyl)ethyl]-1'-propylurea (3) and its undesired isomer 1-cyanoacetyl-1-[2-(4-(dimethylamino) methylphenyl)ethyl]-1'-propylurea. This material is dissolved in 2.2 L of hot ethyl acetate to which ca. 750 mL of hexanes were added to the cloud point and the mixture is allowed to cool to room temperature to induce crystallization. Filtration of the solid and air drying yielded 363 gm of 1'-cyanoacetyl-1-[2-(4-nitrophenyl)ethyl]-1'-propylurea (3). If needed, additional recrystallizations from ethyl acetate-hexanes could be carried out to provide pure 1'-cyanoacetyl-1-[2-(4-(dimethylamino)methylphenyl)ethyl]-1'-propylurea (3).

Step c: Conversion of 1'-Cyanoacetyl-1-[2-(4-(dimethylamino)methylphenyl)ethyl]-1'-propylurea (3) to 6-Amino-1-[2-(4-(dimethylamino)methylphenyl)ethyl]-3-propyluracil (4)

A mixture of ca. 2N sodium hydroxide is produced by dissolving 336 gm of solid sodium hydroxide in 4.2 L of water. To this warm solution is added, in portions, 315 gm of 1'-cyanoacetyl-1-[2-(4-(dimethylamino)methylphenyl) ethyl]-1'-propylurea (3) and the mixture is stirred for 1 hour at 80 degrees C., then is cooled to room temperature with stirring to induce crystallization. The solids were isolated by filtration, washed with four 500 mL portions of water and vacuum dried at 65 degrees C. to yield crude 6-amino-1-[2-(4-(dimethylamino)methylphenyl)ethyl]-3-propyluracil (4).

Step d: Conversion of 6-Amino-1-[2-(4-(dimethylamino)methylphenyl)ethyl]-3-propyluracil (4) to 6-Amino-5-nitroso-1-[2-(4-nitrophenyl)ethyl]-3-propyluracil (5)

To a solution of 235 gm of crude 6-amino-1-[2-(4-(dimethylamino)methylphenyl)ethyl]-3-propyluracil (4), 4.0 L of water and ca. 2.0 L of ethanol at 80 degrees C. is added 55 gm of sodium nitrite in one portion, followed by the dropwise addition of 100 mL of glacial acetic acid. After stirring at 80 degrees C. for 20 minutes the mixture is allowed to cool to near room temperature, then is chilled in an ice bath to effect crystallization. The solids are isolated by filtration, washed with two 1.0 L portions of water and dried under vacuum to yield of 6-amino-5-nitroso-1-[2-(4-(dimethylamino)methylphenyl)ethyl]-3-propyluracil (5).

Step e: Conversion of 6-Amino-5-nitroso-1-[2-(4-(dimethylamino)methylphenyl)ethyl]-3-propyluracil (5) to 5,6-Diamino-1-[2-(4-(dimethylamino)methylphenyl)ethyl]-3-propyluracil (6)

A mixture of 245 gm of 6-amino-5-nitroso-1-[2-(4-(dimethylamino)methylphenyl)ethyl]-3-propyluracil (5), and 2.1 L of water is heated to reflux and 528 mL of a 50% aqueous solution of ammonium sulfide is added with stirring to control foaming. The dark solution is stirred at 90-100 degrees C. for 30 min. and allowed to cool with stirring for 1.5 hours. The mixture is then chilled in an ice bath to fully effect crystallization. The solids are isolated by filtration, washed with three 500 mL portions of water and dried under vacuum to yield 219 gm of a dark solid. This material is recrystallized from 1.0 L of acetonitrile to yield two crops 5,6-diamino-1-[2-(4-(dimethylamino)methylphenyl)ethyl]-3-propyluracil (6).

Example 2

Synthesis of 8-cyclopentylmethyl-3-[2-(4-(dimethyl-amino)phenyl)ethyl]-1-propylxanthine (9)

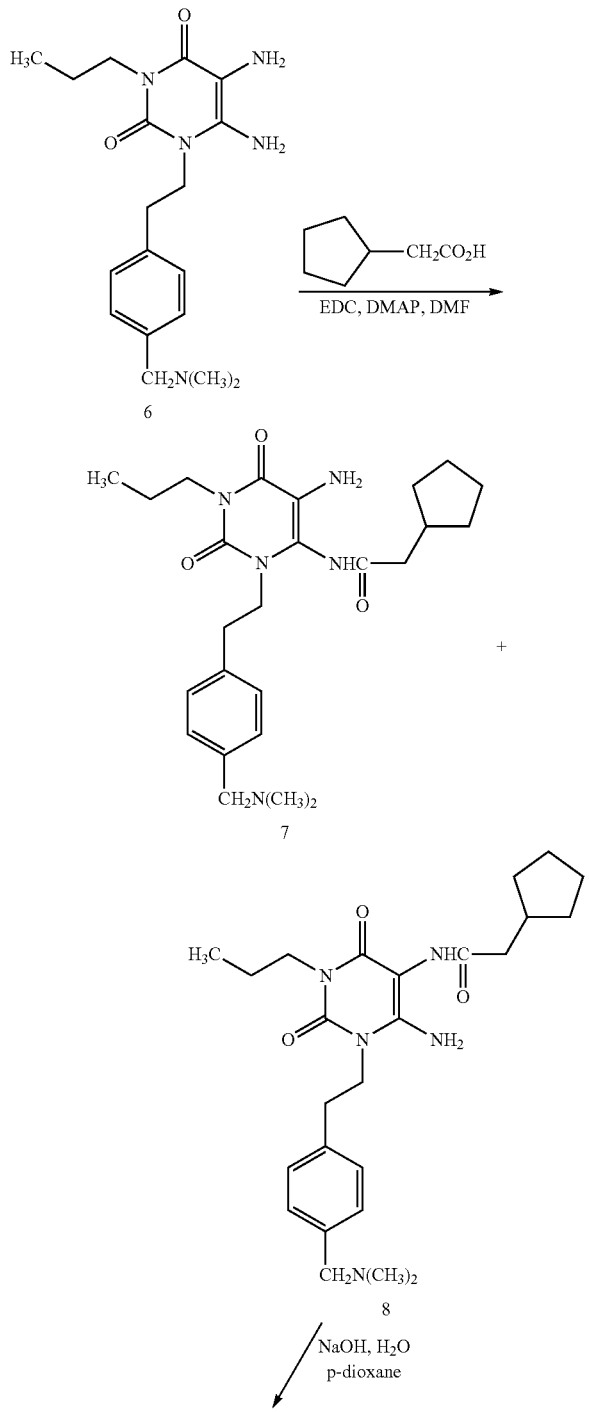

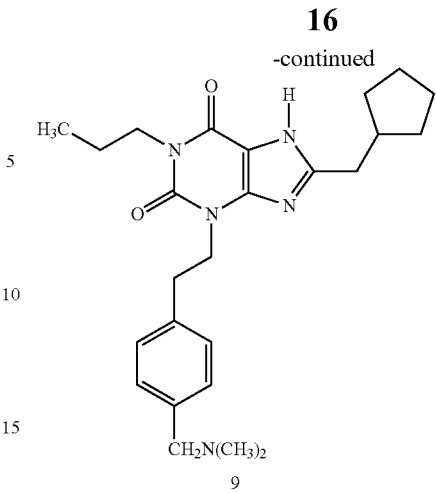

A solution of 45 gm of cyclopentylacetic acid in 630 mL of dimethylformamide (DMF) is chilled in an ice water bath and 63.38 gm of 1-(3-dimethylaminopropyl)-3-ethylcarbodiimide hydrochloride (EDC) is added followed by 5.24 gm of 4-dimethylaminopyridine (DMAP). This mixture is stirred at ca. 4 degrees C. for 30 minutes and 100 gm of 5,6-diamino-1-[2-(4-(dimethylamino)phenyl)ethyl]-3-propyluracil (6) is added in one portion. This mixture is stirred for 60 hr at room temperature. The homogeneous solution is poured into 700 mL of ice water with stirring to effect precipitation. The solids are isolated by filtration, washed with three 100 mL portions of water and dried under vacuum to yield a mixture of 5-amino-1-[2-(4-(dimethylamino)phenyl)ethyl]-6-cyclopentylacetoamino-3-propyluracil (7) and 6-amino-1-[2-(4-(dimethylamino)phenyl)ethyl]-5-cyclopentylacetoamino-3-propyluracil (8) intermediates. These solids are dissolved in 450 mL of p-dioxane, 600 mL of 2N aqueous sodium hydroxide is added and the mixture is heated at reflux for one hr. The solution is then chilled in an ice water bath and the pH adjusted to pH 4 with ca. 100 mL of concentrated hydrochloric acid to yield a precipitate. The solids are isolated by filtration, washed with three 100 mL portions of water and dried under vacuum to yield 82 gm of an orange solid. Recrystallization from hot ethyl acetate afforded 58.0 gm of 8-cyclopentylmethyl-3-[2-(4-(dimethylamino)phenyl)ethyl]-1-propylxanthine (9).

Example 3

Pharmaceutical Formulations (A) Tablet

|  | Amount per Tablet |
| --- | --- |
| Active Ingredient: Compound of Formula (I) | 150 mg |
| Starch | 50 mg |
| Microcrystalline cellulose | 45 mg |
| Polyvinylpryrrolidone (as 10% solution in water) | 5 mg |
| Sodium carboxymethyl starch | 5 mg |
| Magnesium stearate | 1 mg |
| Talc | 1 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed in a tablet machine to yield tablets.

(B) Capsule

|  | Amount per Capsule |
|---|---|
| Active Ingredient: Compound of Formula (I) | 150 mg |
| Starch | 24 mg |
| Microcrystalline cellulose | 24 mg |
| Magnesium stearate | 2 mg |

The active ingredient, cellulose, starch and magnesium stearate are blended, passed through a No. 45 mesh U.S. Sieve, and filed into hard gelatin capsules.

(C) Intravenous Fluid

|  | Amount per bag |
|---|---|
| Active Ingredient: Compound of Formula (I) | 100 mg |
| Sterile Isotonic saline for injection | 250 ml |

In a sterile environment, the active ingredient is dissolved in the isotonic saline and the resulting solution is passed through a 2 micron filter then filed into sterile intravenous fluid bags that are immediately sealed.

In the specification above, there have been disclosed embodiments of the invention and, although specific terms are employed, they are used in a generic and descriptive sense only and not for purposes of limitation of the scope of the invention being set forth in the following claims.

What is claimed is:

1. A compound of formula (I):

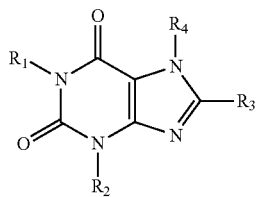

wherein;
$R_1$ is $C_{2-8}$ straight or branched, optionally unsaturated, hydrocarbon moiety optionally substituted with one or more $OR_5$, $NR_5R_6$, $SO_3H$, $PO_3H_2$, $COOR_7$, $NR_8R_9$, $NR_{10}COR_{11}$, $Alk_1COOR_{12}$, $SO_2R_{13}$, $Alk_2NR_{14}R_{15}$, $Alk_3OH$, or halogen groups,
wherein
$R_5$ to $R_{15}$ are independently H or $C_{1-8}$ straight or branched, optionally unsaturated, hydrocarbon chain,
$Alk_1$ through $Alk_3$ are independently $C_{1-8}$ straight or branched alkylene or alkenylene;
$R_2$ is $L_1G_1$,
wherein;
$L_1$ is a $C_{1-2}$ or $C_{4-20}$ straight or branched, optionally unsaturated, hydrocarbon chain moiety;
$G_1$ is a H, $OR_{16}$, $NR_{17}R_{18}$, $PO_3H_2$, $CONR_{19}R_{20}$, $COOR_{21}$, $NR_{22}COAlk_4NR_{23}R_{24}$, $NR_{25}COAlk_5NR_{26}Alk_6NR_{27}R_{28}$, $OCOC_6H_4SO_2F$, $NHCOC_6H_4SO_2F$; or a $C_{3-11}$ hydrocarbon, optionally bridged, optionally aromatic, optionally unsaturated, ring optionally substituted with one or more groups selected from $SO_3H$, $PO_3H_2$, halogen, $OR_{29}$, $COOR_{30}$, $NO_2$, $NR_{31}R_{32}$, $NR_{33}COR_{34}$, $NR_{35}COAlk_7NR_{36}R_{37}$, $NR_{38}COAlk_8CONR_{39}Alk_9NR_{40}R_{41}$, $NR_{42}COAlk_{10}COORAlk_{11}NR_{43}R_{44}$, $Alk_{12}NR_{45}COAlk_{13}NR_{46}R_{47}$, $Alk_{14}NR_{48}COAlk_{15}CONR_{40}Alk_{16}NR_{50}R_{51}$, $Alk_{17}COOR_{52}$, $Alk_{18}COAlk_{19}NR_{53}R_{54}$, $SO_2R_{55}$, $SO_2F$, $Alk_{20}OR_{56}$, $Alk_{21}NR_{57}R_{58}$, $Alk_{22}COAlk_{23}CONR_{59}Alk_{24}NR_{60}R_{61}$ or $Alk_{25}COOR_{62}$;
wherein;
$Alk_4$-$Alk_{25}$ are independently $C_{1-8}$ straight or branched alkylene or alkenylene;
$R_{16}$-$R_{62}$ are independently H or $C_{1-8}$ straight or branched alkyl;
$R_3$ is $L_2G_2$,
wherein;
$L_2$ is a $C_1$ or $C_{3-8}$ straight optionally unsaturated, hydrocarbon moiety optionally substituted with one or more, water soluble, polar groups selected from $OR_{63}$, $NR_{64}R_{65}$, $SO_3H$, $PO_3H_2$, $COOR_{66}$, $NR_{67}R_{68}NR_{69}COR_{70}$, $Alk_{26}COOR_{71}$, $SO_2R_{72}$, $Alk_{27}NR_{73}R_{74}$, $Alk_{28}OH$, or halogen; and
when $L_2$ is $C_{3-8}$, $L_2$ may be intraspersed with one or more hetero atoms;
$G_2$ is one or two $C_{4-5}$ or $C_{7-11}$ non-aromatic, non-bridged, cyclic hydrocarbons, which independently may have one or more carbon atoms substituted with a hetero atom, and which may be optionally substituted with one or more groups selected from $SO_3H$, $PO_3H_2$, halogen, $OR_{75}$, $COOR_{76}$, $NO_2$, $NR_{77}COR_{78}$, $Alk_{29}COOR_{79}$, $SO_2R_{80}$, $Alk_{30}NR_{81}R_{82}$, H, $Alk_{31}OH$, $NR_{85}CONR_{86}R_{87}$, $Alk_{34}H$, or $NR_{88}R_{89}$;
wherein;
$Alk_{26}$-$Alk_{34}$ are independently $C_{1-8}$ straight or branched alkylene or alkenylene, $R_{63}$-$R_{89}$ are independently H or $C_{1-8}$ straight or branched alkyl;
$R_4$ is $C_m$ alkyl, $Alk_{36}COOR_{90}$, $Alk_{37}CONR_{91}R_{92}$, $Alk_{39}SO_3H$, $Alk_{40}PO_3H_2$, $Alk_{41}OR_{93}$, $Alk_{43}NR_{94}R_{95}$, or $Alk_{44}NR_{96}Alk_{45}OH$; and $R_4$ may also be H or methyl when $G_2$ is one $C_{4-5}$ or two $C_{10-11}$ non-aromatic, non-bridged, cyclic hydrocarbons,
wherein;
$Alk_{35}$ through $Alk_{45}$ are independently $C_{1-8}$ straight or branched alkylene or alkenylene;
$R_{90}$ through $R_{96}$ are independently H or $C_{1-8}$ straight or branched alkyl; and
when $R_4$ is other than H, methyl, alkyl, $Alk_{36}COOR_{90}$, $Alk_{39}SO_3H$, or $Alk_{41}OR_{93}$, $G_2$ may include bridged cyclic hydrocarbons; and
salts thereof.

2. The compound of claim 1 wherein:
$R_1$ is $C_{2-4}$ straight or branched alkylene optionally substituted with $OR_5$, $NR_5R_6$, or $COOR_7$,
$L_1$ is a $C_{1-2}$ or $C_{4-8}$ straight or branched alkylene,
$G_1$ is H, $OR_{16}$, $NR_{17}R_{18}$, $CONR_{19}R_{20}$, $COOR_{21}$, $OCOC_6H_4SO_2F$, or $NHCOC_6H_4SO_2F$; or a $C_{3-11}$ hydrocarbon, optionally bridged, optionally aromatic, optionally unsaturated, ring,
$L_2$ is a $C_1$ or $C_{3-8}$ straight hydrocarbon chain,
$G_2$ is a $C_{4-5}$ or $C_{10-11}$ non-aromatic, non-bridged, cyclic hydrocarbon,
$R_4$ is H, $Alk_{40}PO_3H_2$, $Alk_{43}NR_{94}R_{95}$, or $Alk_{44}NR_{96}Alk_{45}OH$.

3. The compound of claim 2 wherein:
   $R_1$ is $C_{2-4}$ straight or branched hydrocarbon moiety,
   $L_1$ is ethylene or butylene,
   $G_1$ is H, cyclopropyl, cyclopentyl, cyclohexyl, cyclohexenyl bornyl, norbornyl, adamantyl, noradamantyl, bicyclooctyl, phenyl, naphthyl, $OCOC_6H_4SO_2F$, or $NHCOC_6H_4SO_2F$
   $L_2$ is methylene or propylene,
   $G_2$ is cyclopentyl or decalin,
   $R_4$ is H or $Alk_{44}NR_{96}Alk_{45}OH$.

4. The compound of claim 1 which further comprises a pharmaceutically acceptable carrier thereof.

* * * * *